United States Patent
Bashiardes et al.

(10) Patent No.: US 6,392,042 B1
(45) Date of Patent: May 21, 2002

(54) POLYHYDROXYALKYLPYRAZINE DERIVATIVES, THEIR PREPARATION AND MEDICAMENTS COMPRISING THEM

(75) Inventors: Georges Bashiardes, Poitiers; Jean-Christophe Carry, Meudon; Michel Evers, La Queue en Brie; Bruno Filoche, Creteil; Serge Mignani, Chatenay-Malabry, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/480,965

(22) Filed: Jan. 14, 2000

Related U.S. Application Data

(63) Continuation of application No. PCT/FR98/01544, filed on Jul. 15, 1998.

(30) Foreign Application Priority Data

Jul. 17, 1997 (FR) .............................................. 97 09060

(51) Int. Cl.$^7$ ..................... C07D 241/00; A61K 31/495
(52) U.S. Cl. ..................... 544/358; 544/398; 514/252.1
(58) Field of Search ....................... 514/252.1; 544/358, 544/398

(56) References Cited

FOREIGN PATENT DOCUMENTS

| JP | 45029990 | * | 9/1970 |
| WO | WO 97 22813 | | 8/1997 |

OTHER PUBLICATIONS

Hardt et al., "Curie–Point Pyrolysis—Capillary Gas Chromatography—Mass Spectrometry of Polyhydroxyalkylpyrazines," J. Anal. Appl. Pyrolysis, 13(3), 191–8 (1988).
Nishie et al., "Pharmacology of Alkyl and Hydroxyalkylpyrazines," Toxicol. Appl. Pharmacol., 17(1) 244–9 (1970).
Tsuchida et al., "Identification of Novel Non–Volatile Pyrazines in Commercial Caramel Colors," Dev. Food Sci., 13 (Amino–Carbonyl React. Food Biol. Syst.), 85–94 (1986).
Eitelman et al., Decomposition Reactions of Amino Sugars: The Dehydration of 2–amino-2–deoxy–D–glucose, Carbohydr. Res., 77, 205–11 (1979).
Amino–sugar synthesis–(XXIV) pyrazine form.from amino–sug.K.Richard et al.,Ann.644,117, Jan. 1961.*
"Formatn.of deoxyfructozine & its 6–isom . . . "T.Hironobu et al.Agric.Biol.Chem.40/5,921, Jan. 1961.*
Nishie et al., Pharmacology of Alkyl and Hydroxyalklpyrazines, J. Toxic. App. Pharm. 17:244–249 (1970).
Hardt et al., Curie–Point pyrolysis–capillary gas chromatography–mass spectrometry of polyhydroxyalkylpyrazines, J. Anal. App. Pyrol. 13:191–198 (1988).
Eitelman et al., Decomposition reactions of amino sugars: the dehydration of 2–amino-2–deoxy–D–glucose, Carbohydrate Research 77:205–211 (1979).
Tsuchida et al., Identificatiion of Novel Non–volatile pyrazines in commerical carmel colors, Dev. Food Sci. 13:85 (1986).
PCT/FR98/01544: International Preliminary Examination Report.
PCT/FR98/01544: International Search Report.

* cited by examiner

*Primary Examiner*—Richard L. Raymond
*Assistant Examiner*—Sudhaker B. Patel
(74) *Attorney, Agent, or Firm*—Irving Newman

(57) ABSTRACT

A pharmaceutical composition containing at least one stereoisomer of at least one compound selected from:

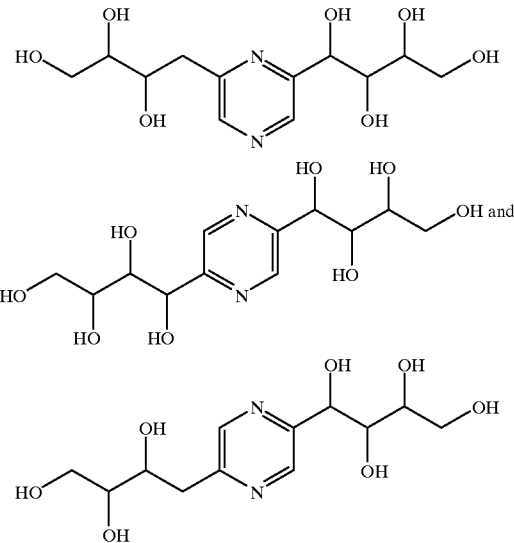

Or a salt thereof with an organic or inorganic acid.

8 Claims, No Drawings

POLYHYDROXYALKYLPYRAZINE DERIVATIVES, THEIR PREPARATION AND MEDICAMENTS COMPRISING THEM

This application is a continuation of PCT/FR98/01544 filed Jul. 15, 1998.

The present invention relates to medicaments comprising, as active principle, at least one compound of general formula:

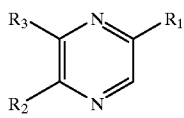
(I)

in their stereoisomeric forms or their salts with an inorganic or organic acid, to novel compounds of formula (I) or their salts with an inorganic or organic acid, and to their preparation.

In the general formula (I):

$R_1$ represents the stereoisomeric forms of the chain

—(CHOH)$_3$—CH$_2$OH (II)

and either $R_2$ represents a hydrogen atom and $R_3$ represents the stereoisomeric forms of the chain

—CH$_2$—(CHOH)$_2$—CH$_2$OH (III)

or $R_2$ represents the stereoisomeric forms of the chains

—(CHOH)$_3$—CH$_2$OH (II)

or

—CH$_2$—(CHOH)$_2$—CH$_2$OH (III)

and $R_3$ represents a hydrogen atom with the exception of fructosazine of formula

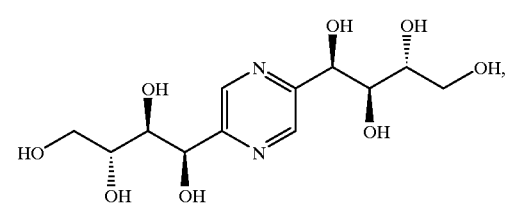
(IV)

deoxyfructosazine of formula

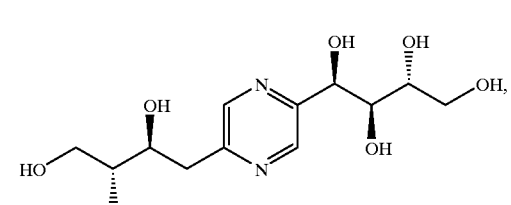
(V)

and the compound of formula

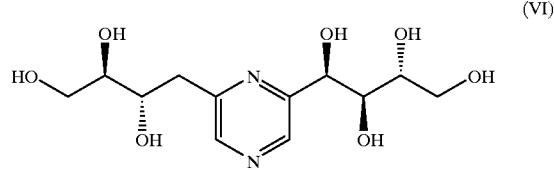
(VI)

The medicaments according to the invention thus comprise at least one stereoisomer of the following compounds:

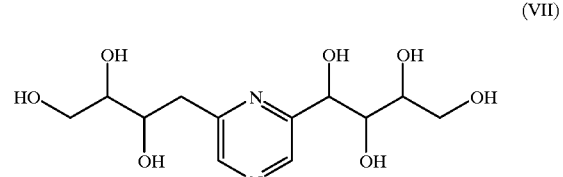
(VII)

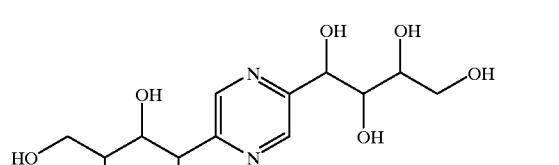
(VIII)

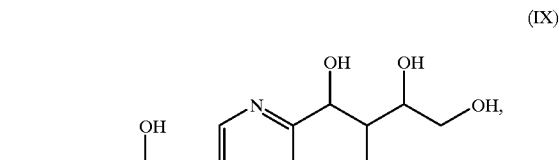
(IX)

or a salt of such a compound with an organic or inorganic acid, with the exception of fructosazine, deoxyfructosazine and the compound of formula (VI).

The medicaments according to the invention are preferably those which comprise, as active principle, at least one compound of formula (I) chosen from the following compounds:

1-[5-(1R,2R,3R,4-tetrahydroxybutyl)pyrazin-2-yl]butane-1R,2R,3R,4-tetraol

1-[5-(1R,2R,3S,4-tetrahydroxybutyl)pyrazin-2-yl]butane-1R,2R,3S,4-tetraol

1-[5-(1R,2S,3S,4-tetrahydroxybutyl)pyrazin-2-yl]butane-1R,2S,3S,4-tetraol

1-[5-(1S,2R,3R,4-tetrahydroxybutyl)pyrazin-2-yl]butane-1S,2R,3R,4-tetraol

1-[5-(1S,2R,3S,4-tetrahydroxybutyl)pyrazin-2-yl]butane-1S,2R,3S,4-tetraol

1-[5-(1S,2S,3R,4-tetrahydroxybutyl)pyrazin-2-yl]butane-1S,2S,3R,4-tetraol

1-[5-(1S,2S,3S,4-tetrahydroxybutyl)pyrazin-2-yl]butane-1S,2S,3S,4-tetraol

1-[5-(2R,3R,4-trihydroxybutyl)pyrazin-2-yl]butane-1R,2R,3R,4-tetraol

1-[5-(2R,3S,4-trihydroxybutyl)pyrazin-2-yl]butane-1R,2R,3S,4-tetraol

1-[5-(2S,3S,4-trihydroxybutyl)pyrazin-2-yl]butane-1R,
2S,3S,4-tetraol

1-[5-(2R,3R,4-trihydroxybutyl)pyrazin-2-yl]butane-1S,
2R,3R,4-tetraol

1-[5-(2R,3S,4-trihydroxybutyl)pyrazin-2-yl]butane-1S,
2R,3S,4-tetraol

1-[5-(2S,3R,4-trihydroxybutyl)pyrazin-2-yl]butane-1S,
2S,3R,4-tetraol

1-[5-(2S,3S,4-trihydroxybutyl)pyrazin-2-yl]butane-1S,
2S,3S,4-tetraol

1-[6-(2R,3R,4-trihydroxybutyl)pyrazin-2-yl]butane-1R,
2R,3R,4-tetraol

1-[6-(2R,3S,4-trihydroxybutyl)pyrazin-2-yl]butane-1R,
2R,3S,4-tetraol

1-[6-(2R,3R,4-trihydroxybutyl)pyrazin-2-yl]butane-1S,
2R,3R,4-tetraol

1-[6-(2R,3S,4-trihydroxybutyl)pyrazin-2-yl]butane-1S,
2R,3S,4-tetraol

1-[6-(2S,3R,4-trihydroxybutyl)pyrazin-2-yl]butane-1S,
2S,3R,4-tetraol

1-[6-(2S,3S,4-trihydroxybutyl)pyrazin-2-yl]butane-1S,
2S,3S,4-tetraol or a salt of such a compound with an inorganic or organic acid, and, more advantageously still, those which comprise, as active principle, at least one compound of formula (I) chosen from the following compounds:

1-[5-(1R,2R,3R,4-tetrahydroxybutyl)pyrazin-2-yl]
butane-1R,2R,3R,4-tetraol

1-[5-(2R,3R,4-trihydroxybutyl)pyrazin-2-yl]butane-1R,
2R,3R,4-tetraol

1-[5-(2S,3R,4-trihydroxybutyl)pyrazin-2-yl]butane-1S,
2S,3R,4-tetraol

1-[6-(2R,3S,4-trihydroxybutyl)pyrazin-2-yl]butane-1S,
2R,3S,4-tetraol

1-[6-(2R,3R,4-trihydroxybutyl)pyrazin-2-yl]butane-1R,
2R,3R,4-tetraol or a salt of such a compound with an inorganic or organic acid.

The following compounds are known:

fructosazine, deoxyfructozasine and the compound of formula (VI) are described (Patent JP 43-13469, Ann., 644, 122–127 (1961); Agr. Biol. Chem., 39 (5), 1143–1148 (1975)), the stereoisomers of general formula (VIa), (VIb), (VIc) and (VId) mentioned hereinbelow have been described (Patent JP 43-13469, Carbohyd. Res., 26(2), 377–84 (1973), J. Anal. Appl. Pyrolysis, 13, 191–198(1988))

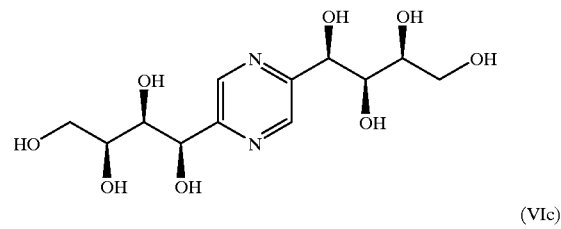

(VIa)

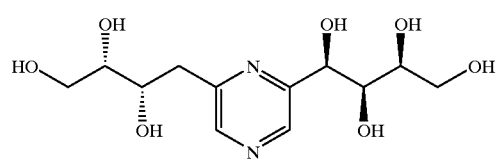

(VIb)

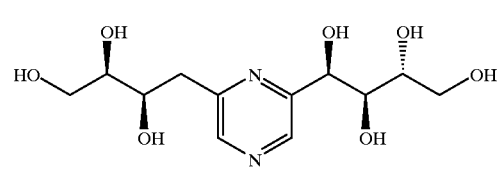

(VIc)

the compounds of general formulae (VII), (VIII) and (IX) resulting from glucose, fructose, mannose and galactose have been described in Japanese Patent JP 53-90401.

However, their use as medicament has not been mentioned and this is the subject matter of the present invention.

The compounds of formula (I) or their salts with an inorganic or organic acid, with the exception of the following compounds:

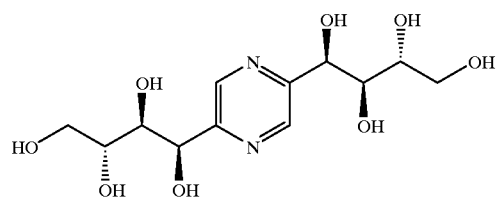

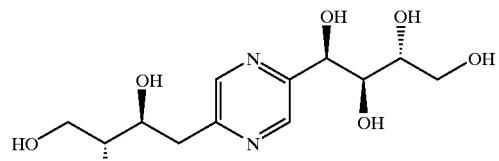

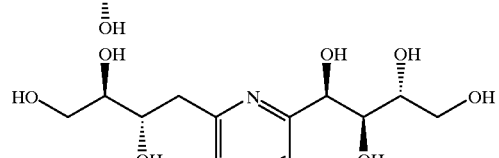

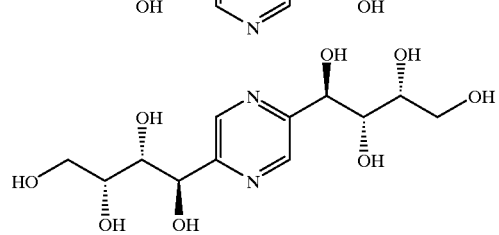

(VId)

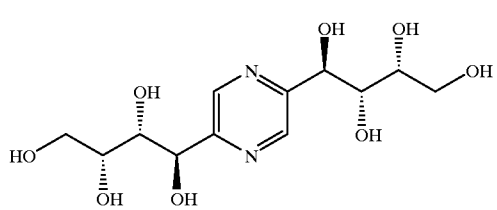

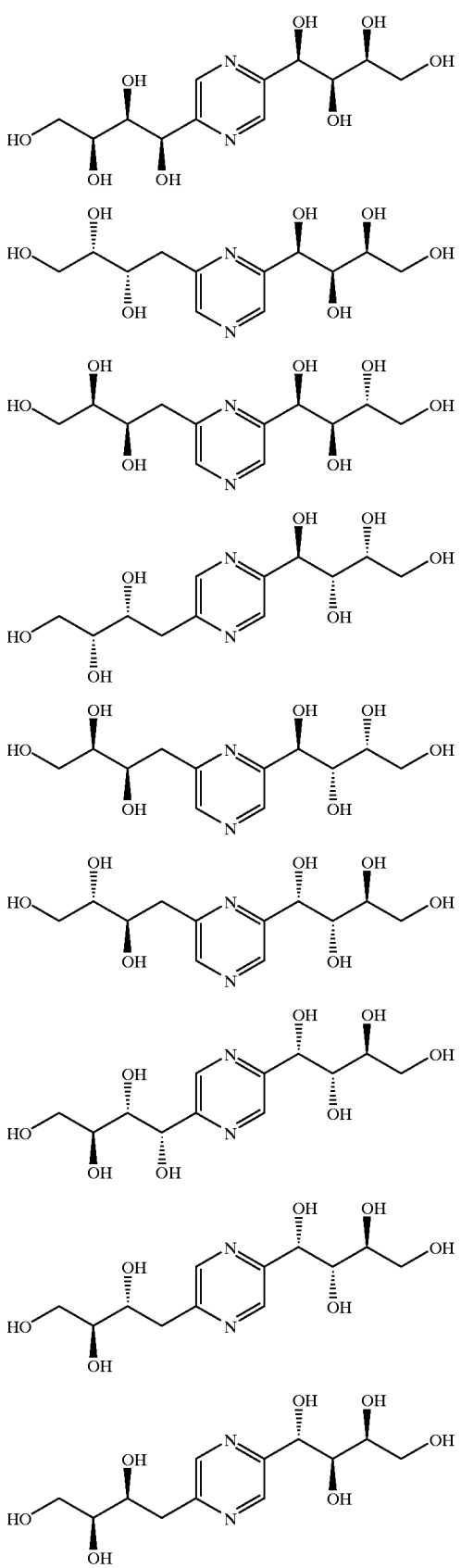

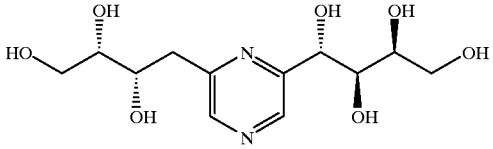

are novel and, as such, form part of the invention.

The preferred compounds of formula (I) are the following:

1-[5-(1R,2R,3S,4-tetrahydroxybutyl)pyrazin-2-yl]butane-1R,2R,3S,4-tetraol

1-[5-(1S, 2R, 3R, 4-tetrahydroxybutyl)pyrazin-2-yl]butane-1S,2R,3R,4-tetraol

1-[5-(1S,2S,3R,4-tetrahydroxybutyl)pyrazin-2-yl]butane-1S,2S,3R,4-tetraol

1-[5- (1S, 2S,3S, 4-tetrahydroxybutyl)pyrazin-2-yl butane-1S,2S,3S,4-tetraol

1-[5-(2R,3S,4-trihydroxybutyl)pyrazin-2-yl]butane-1R,2R,3S,4-tetraol

1-[5-(2S,3S,4-trihydroxybutyl)pyrazin-2-yl]butane-1R,2S,3S,4-tetraol

1-[5-(2R,3R,4-trihydroxybutyl)pyrazin-2-yl]butane-1S,2R,3R,4-tetraol

1-[5-(2S,3R,4-trihydroxybutyl)pyrazin-2-yl]butane-1S,2S,3R,4-tetraol

1-[6-(2R,3S,4-trihydroxybutyl)pyrazin-2-yl]butane-1R,2R,3S,4-tetraol

1-[6-(2R,3R,4-trihydroxybutyl)pyrazin-2-yl]butane-1S,2R,3R,4-tetraol

1-[6-(2S,3R,4-trihydroxybutyl)pyrazin-2-yl]butane-1S,2S,3R,4-tetraol or a salt of such a compound with an inorganic or organic acid, advantageously 1-[5-(2S,3S,4-trihydroxybutyl)pyrazin-2-yl]butane-1R,2S,3S,4-tetraol 1-[5-(2R,3R,4-trihydroxybutyl)pyrazin-2-yl]butane-1S,2R,3R,4-tetraol 1-[5-(2S,3R,4-trihydroxybutyl)pyrazin-2-yl]butane-1S,2S,3R,4-tetraol or a salt of such a compound with an inorganic or organic acid, and, more advantageously still, the following compound:

1-[5-(2S,3R,4-trihydroxybutyl)pyrazin-2-yl]butane-1S,2S,3R,4-tetraol or a salt of such a compound with an inorganic or organic acid.

The stereoisomeric forms of the compounds of general formula (I) are obtained from the stereoisomeric forms of the reactants hereinbelow used by the preparation process according to the invention.

The stereoisomers of the compounds of formula (I) in which $R_1$ represents the stereoisomeric forms of the —(CHOH)$_3$—CH$_2$OH chain (II), $R_2$ represents a hydrogen atom and $R_3$ represents the stereoisomeric forms of the —CH$_2$—(CHOH)$_2$—CH$_2$OH chain (III), that is to say the compounds represented by the general formula (VII), can be obtained by reaction of ammonium formate with an aldose, or a mixture of 2 aldoses, of the dextrorotatory or laevorotatory series, of general formula:

CHO—CHOH—R$_1$  (X)

in which $R_1$ has the same meaning as in the formula (I).

This reaction can preferably be carried out at a temperature of between 15° C. and 100° C., preferably in aqueous medium.

The aldoses are commercially available or can be obtained from:
a) commercially available aldoses:
by epimerization reactions, by application or adaptation of the methods described in Adv. Carbohydr. Chem., 13, 63, (1958), in particular in basic medium by means of a dilute aqueous sodium hydroxide solution (0.03 to 0.05%), at a temperature of between 20 and 40° C.,
by chain-extension reactions, by application or adaptation of the methods described in "The Carbohydrates", edited by W. Pigman and D. Horton, Academic Press, New York, Volume IA, 133 (1972), and in particular by forming the cyanohydrin of the starting aldose (for example, by reaction with sodium cyanide in aqueous solution, at a temperature of between 10 and 30° C. and in the presence of sodium hydroxide, at a pH in the region of 9), then hydrolysis of the nitrile functional group thus formed to the corresponding acid by application or adaptation of the methods described in Organic Synthesis, Volume I, page 436 and Volume III, page 85 (for example, using concentrated sulphuric acid or hydrochloric acid, in aqueous solution, at a temperature of between 20° C. and the reflux temperature of the reaction mixture), and then reduction of the carboxylic acid functional group to the corresponding aldehyde by application or adaptation of the methods described in J. Am. Chem. Soc., 71, 122 (1949), in particular using an alkali metal borohydride (for example, sodium borohydride), in aqueous solution, at a temperature of between 20° C. and the boiling temperature of the reaction mixture,
by chain-shortening reactions, by application or adaptation of the methods described in "The Carbohydrates", edited by W. Pigman and D. Horton, Academic Press, New York, Volume IB, 1980, page 929 or Chem. Ber., 83, 559 (1950) and in particular by converting the aldehyde functional group of the aldose to the corresponding hydroxylamine by application or adaptation of the methods described in Organic Synthesis, Volume II, page 314 (for example, using hydroxylamine hydrochloride, in aqueous solution and in the presence of a base, such as sodium carbonate, at a temperature of between 20 and 50° C.), and then reaction with 3,4-dinitrofluorobenzene in the presence of carbon dioxide and a base, such as sodium hydrogencarbonate, in aqueous solution, and an aliphatic alcohol (for example, isopropyl alcohol), at a temperature of between 50 and 80° C.,
b) corresponding allyl alcohols, by application or adaptation of the methods described in Science, 220, 949 (1983) and in particular using tert-butyl hydroperoxide in the presence of a titanium(IV) complex, such as the titanium(IV) isopropoxide and optically pure dialkyl tartrate (for example, diethyl tartrate) complex, followed by successive reaction with sodium thiophenolate, para-chloroperbenzoic acid in acetic anhydride, and diisopropylaluminium hydride.

The stereoisomers of the sugar of formula (X) can be those of aldoses containing 6 carbon atoms; those preferably used are D-gulose, D-galactose, D-allose, D-altrose, D-idose, D-talose, L-glucose, L-mannose, L-galactose, L-allose, L-altrose, L-idose, L-talose or L-gulose.

The stereoisomers of the compounds of formula (I) in which $R_1$ represents the stereoisomeric forms of the —(CHOH)$_3$—CH$_2$OH chain (II), $R_2$ represents the stereoisomeric forms of the —(CHOH)$_3$—CH$_2$OH chains (II) and R represents a hydrogen atom, that is to say compounds represented by the general formula (VIII), can be obtained by treatment, in basic medium, of an aminoaldose, or of a mixture of 2 aminoaldoses, of general formula:

optionally in the form of an addition salt, such as the hydrochloride, in which $R_1$ has the same meaning as in the general formula (I).

The reaction is preferably carried out at a temperature in the region of 20° C. and use is preferably made of an aqueous ammonia solution and more particularly a 28% solution.

The aminoaldoses of formula (XI) are commercially available or can be prepared by application or adaptation of methods described in, for example:
(a) Methods Carbohydr. Chem., 7, 29 (1976), which consist in converting the aldehyde functional group of the corresponding aldose to a nitroethylene group using nitromethane in basic medium (for example, sodium ethoxide) and in then successively treating the product obtained with a saturated aqueous ammonia solution, at a temperature of between 20° C. and. 30° C., with Ba(OH)$_2$ in aqueous solution, at a temperature of between 20° C. and 30° C., and finally [lacuna] dilute sulphuric acid (10 to 15%), at a temperature of between 20° C. and 30° C.,
(b) "The Amino Sugar", edited by R. W. Jeanloz, Academic Press, New York, 1969, page 1 or "The Carbohydrates", edited by W. Pigman and D. Horton, Academic Press, New York, Volume IB, 1980, page 664, which consist in converting the aldehyde functional group of the corresponding aldose to an imino group from a primary aromatic amine (for example aniline) and of subsequently successively reacting [lacuna] hydrocyanic acid, at a temperature of between 0° C. and 20° C., and [lacuna] hydrogen in the presence of palladium, in a solvent such as an ether (for example tetrahydrofuran) or an aliphatic alcohol (for example, ethanol or methanol), at a temperature of between 20° C. and 50° C.

The stereoisomers of the aminoaldose of formula (XI) can be those of aminoaldose comprising 6 carbon atoms; that preferably used is D-galactosamine, optionally in the form of an addition salt, such as the hydrochloride.

The stereoisomers of the compounds of formula (I) in which $R_1$ represents the stereoisomeric forms of the —(CHOH)$_3$—CH$_2$OH chain (II), $R_2$ represents the stereoisomeric forms of the —CH$_2$—(CHOH)$_2$—CH$_2$OH chains (III) and $R_3$ represents a hydrogen atom, that is to say compounds represented by the general formula (IX), can be obtained
either from an aminoaldose, or from a mixture of 2 aminoaldoses, of general formula:

in which $R_1$ has the same meaning as in the general formula (I), in acidic medium and more particularly in acetic acid medium and preferably while carrying out the reaction at a temperature of between 15° C. and 100° C., or from a ketose, or from a mixture of 2 ketoses, of general formula:

$$HOCH_2CO-R_1 \quad (XII)$$

in which $R_1$ has the same meaning as in the general formula (I), by reaction with ammonium formate and preferably while carrying out the reaction at a temperature of between 15° C. and 100° C. and preferably in aqueous medium.

The ketoses of formula (XII) are commercially available or can be prepared by application or adaptation of the methods described in, for example: a) Adv. Carbohydr. Chem., 13, 63, (1958), which consist in reacting the corresponding aldose either with a base, such as calcium hydroxide, sodium hydroxide, pyridine or quinoline, or with an acid, such as sulphuric acid, in aqueous solution or in the pure phase, at a temperature of between 20 and 50° C., b) Tetrahedron Asymmetry, 7(8), 2185, (1996), J. Am. Chem. Soc., 118(33), 7653 (1996), J. Org. Chem., 60(13), 4294 (1995), Tetrahedron Lett., 33(36), 5157 (1992), J. Am. Chem. Soc., 113(17), 6678 (1991), Angew. Chem., 100(5), 737, (1988), J. Org. Chem., 57, 5899 (1992), which consist, for example, in condensing either hydroxypyruvaldehyde, 1,3-dihydroxyacetone, 1,3-dihydroxyacetone monophosphate or hydroxypyruvic acid with a 2-hydroxyacetaldehyde which is substituted in the 2 position and which is optionally optically pure, optionally in the presence of an enzyme, such as a transketolase. This reaction is generally carried out in an aqueous solution, at a temperature of between 20 and 50° C., optionally in the presence of a base (for example, sodium hydroxide), of barium chloride, of magnesium chloride or of zinc chloride. Derivatives possessing a 2-hydroxyacetaldehyde group are commercially available or can be prepared from aldoses by application or adaptation of the methods described in P. Collins and R. Ferrier, Monosaccharides, Their Chemistry and Their Roles in Natural Products, published by J. Wiley (1995), and M. Bols, Carbohydrate Building Blocks, published by J. Wiley (1996).

The stereoisomer of the aminoaldose of formula (XI) preferably used is D-galactosamine.

The stereoisomers of the compounds of formula (XII) can be those of ketoses comprising 6 carbon atoms; those preferably used are D-psicose, D-sorbose, D-tagatose, L-psicose, L-fructose, L-sorbose-or L-tagatose.

The reaction mixtures obtained by the various processes described above are treated according to conventional physical (evaporation, extraction, distillation, chromatography or crystallization, for example) or chemical (formation of salts, for example) methods.

The compounds of formula(I) can optionally be converted to addition salts with an inorganic or organic acid by the action of such an acid in an organic solvent, such as an alcohol, a ketone, an ether or a chlorinated solvent. These salts also form part of the invention.

Mention may be made, as examples of pharmaceutically acceptable salts, of the addition salts with inorganic or organic acids, such as acetate, propionate, succinate, benzoate, fumarate, maleate, oxalate, methanesulphonate, isethionate, theophyllinacetate, salicylate, methylenebis(b-oxynaphthoate), hydrochloride, sulphate, nitrate and phosphate.

The following examples more particularly illustrate the preparation process used according to the invention.

EXAMPLE 1

A solution of 1.0 g of D-sorbose and 3.5 g of ammonium formate in 4 cm³ of water is heated at reflux for 0.5 hour and then allowed to cool to room temperature. The mixture is concentrated under reduced pressure (2.7 kPa) at a temperature in the region of 40° C. The brown residue is taken up successively in ethyl ether and toluene and evaporated to dryness. The new residue is taken up in ethanol and filtered. The filtrate is evaporated to give a brown oil. The operation is repeated several times until there is no longer any precipitate. The residue thus obtained is purified by chromatography on a silica (0.063–0.200 mm) column, elution being carried out with an ethanol/n-butanol/28% aqueous ammonia solution/water 8/2/2/1 by volume mixture. The fractions containing the expected product are combined and concentrated under reduced pressure (2.7 kPa) at a temperature in the region of 40° C. The sticky yellow solid obtained is taken up in a sufficient amount of ethanol/methanol to produce a solution, followed by the addition of ethyl ether until a precipitate begins to appear, which precipitate is filtered. The product crystallizes to give 0.15 g of 1-[5-(2R, 3R,4-trihydroxybutyl)pyrazin-2-yl]butane-1S,2R,3R,4-tetraol in the form of a beige solid which melts at 90° C. [$^1$H N.M.R. spectrum (400 MHz, d6—(CD$_3$)$_2$SO, δ in ppm): 2.85 and 2.93 (2 dd, respectively J=13 and 9 Hz and J=13 and 4 Hz, 2H, 5α CH$_2$), from 3.25 to 3.55 (mt, 6H, 2γ CH, 2δ CH$_2$, 5γ CH and 5γ CH$_2$), 3.76 (mt, 1H, 2β CH) , 3.91 (mt, 1H, 5β CH), from 4.35 to 4.65 (unresolved peak, 6H, OH at 2β, OH at 2γ, OH at 2δ, OH at 5β, OH at 5γ and OH at 5δ), 4.78 (t, J=4.5 Hz, 1H, 2α CH), 5.39 (d, J=4.5 Hz, 1H, OH at 2α), 8.43 (s, 1H, =CH at 6), 8.61 (s, 1H, =CH at 3)·$\alpha_D^{20}$ =+71.3°±1.3 (c=0.5%, MeOH)].

EXAMPLE 2

A suspension containing 1.0 g of D-galactosamine hydrochloride and 0.73 cm³ of diethylamine is left stirring for 1 hour and then filtered. The filtrate is evaporated and dissolved in 10 cm³ of aqueous ammonia solution comprising 28% of ammonia and left stirring at room temperature for three weeks. The mixture is then concentrated under reduced pressure (2.7 kPa) at a temperature in the region of 40° C. to give a yellow oil which is taken up in methanol and filtered. The filtrate is evaporated to give an orange oil which is purified by chromatography on a silica (0.04–0.063 mm) column, elution being carried out with an ethanol/n-butanol/ 28% aqueous ammonia solution/water 8/2/2/1 by volume mixture. The fractions containing the expected product are combined and concentrated under reduced pressure (2.7 kPa) at a temperature in the region of 40° C. to give an orangey-yellow sticky solid. The latter is crystallized from methanol and the solid is filtered to give 0.12 g of 1-[5-(1R, 2R,3R,4-tetrahydroxy-butyl)pyrazin-2-yl]butane-1R, 2R,3R, 4-tetraol in the form of a beige powder which melts at 109° C.
[$^1$H N.M.R. spectrum (400 MHz, d6-(CD$_3$)$_2$SO, δ in ppm): from 3.35 to 3.50 (mt, 4H, 2 8 CH$_2$O and 5δ CH$_2$O), from 3.70 to 3.85 (mt, 4H, 2p CH, 2γ CH, 5p CH and 5γ CH), 4.24 (d, J =8 Hz, 2H, OH at 2β and OH at 5β), 4.41 (d, J=6.5 Hz, 2H, OH at 2γ and OH at 5γ), 4.50 (broad t, J=6 Hz, 2H, OH at 2δ and OH at 5δ), 4.64 (2 dd, J =7 and 6 Hz, 2H, 2α CH and 5α CH), 5.48 (d, J =6 Hz, 2H, OH at 2α and OH at 5α), 8.56 (s, 2H, =CH at 3 and =CH at 6)].

EXAMPLE 3

A solution of 1.0 g of D-tagatose and 3.5 g of ammonium formate in 4 cm³ of water is heated at reflux for 0.5 hour and then allowed to cool to room temperature. The mixture is filtered and the residue concentrated under reduced pressure (2.7 kPa) at a temperature in the region of 40° C. to give a brown residue which is taken up successively in ethanol and ethyl ether and evaporated to dryness. This residue is triturated in ethyl ether and filtered. The brown solid is dissolved in ethanol. Sodium hydroxide is added to this solution to pH 12 and the solution is left stirring for 40 hours; the formation of a precipitate is then observed. The reaction mixture is filtered and the filtrate is concentrated under reduced pressure (2.7 kPa) at a temperature in the region of 40° C. to give a yellow solid which is taken up in methanol/ethyl ether and filtered. After evaporation of the filtrate, the residue is dissolved in methanol and brought to pH 2 by addition of an ethanolic solution of hydrochloric acid. The precipitate which is formed is filtered and the filtrate is concentrated. The residue is purified by chromatography on a silica (0.040–0.063 mm) column, elution being carried out with an ethanol/n-butanol/aqueous ammonia solution/water 8/2/1/1 by volume mixture. The fractions containing the expected product are combined and concentrated under reduced pressure (2.7 kPa) at a temperature in the region of 40° C. The white solid thus obtained is recrystallized from methanol. 90 mg of 1-[5-(2R,3R,4-trihydroxybutyl)-pyrazin-2-yl]butane-1R,2R,3R,4-tetraol are obtained in the form of a white crystalline solid which melts at 146° C.

[$^1$H N.M.R. spectrum (400 MHz, d6-$(CD_3)_2SO$, δ in ppm): 2.86 (dd, J =14 and 9 Hz, 1H, 1H of the 5α $CH_2$), 2.92 (dd, J =14 and 3.5 Hz, 1H, the other H of the 5α $CH_2$), from 3.30 to 3.60 (mt, 5H, 2δ $CH_2O$, 5δ $CH_2O$ and 5γ CH), from 3.70 to 3.85 (mt, 2H, 2γ CH and 2β CH), 3t90 (mt, 1H, 5β CH), 4.22 (d, J=7 Hz, 1H, OH at 2β), 4.38 (d, J=6.5 Hz, 1H, OH at 2γ), 4.43 (d, J=7 Hz, 1H, OH at 5β), from 4.40 to 4.55 (mt, 2H; OH at 2δ and OH at 5δ), from 4.55 to 4.70 (mt, 2H, 2α CH and OH at 5γ), 5.44 (d, J=6 Hz, 1H, OH at 2α), 8.43 (s, 1H,=CH at 6), 8.54 (s, 1H,=CH at 3)·$α_D^{20}$=−14.6°±1.13 (c=0.2%, water)].

EXAMPLE 4

A solution of 10.0 g of L-sorbose and 7.0 g of ammonium formate in 28 cm$^3$ of water is heated at reflux for 2.5 hours and then allowed to cool to room temperature. The mixture is concentrated under reduced pressure (2.7 kPa) at a temperature in the region of 50° C. The brown pasty residue is purified by chromatography on a silica (0.020–0.045 mm) column, elution being carried out with an ethanol/n-butanol/ aqueous ammonia solution/water 8/2/2/1 by volume mixture. The fractions containing the expected product are combined and concentrated under reduced pressure (2.7 kPa) at a temperature in the region of 50° C. The brown oil obtained (9.1 g) is taken up in a mixture of 100 cm$^3$ of ethanol and 10 cm$^3$ of water. The mixture is brought to reflux, treated with 0.9 g of animal charcoal and then filtered on paper. The filtrated is concentrated under reduced pressure (2.7 kPa) at a temperature in the region of 50° C. to give a brown oil (6.2 g). The latter is taken up in a mixture of 50 cm$^3$ of ethanol and 1.5 cm$^3$ of water and recrystallized. The crystals obtained are filtered, pulled dry and then washed with the same mixture. After drying to constant weight, 0.86 g of 1-[5-(2S,3S,4-trihydroxybutyl)-pyrazin-2-yl]butane-1R,2S,3S,4-tetraol is obtained in the form of a beige crystalline solid melting at 116° C.

$^1$H N.M.R. spectrum (400 MHz, d6-$(CD_3)_2SO$ , δ ppm): 2.87 (limit AB, 2H, 5α $CH_2$), from 3.30 to 3.60 (mt, 6H, 2γ CH, 2δ $CH_2O$, 5γ CH and 5δ $CH_2O$), 3.76 (mt, 1H, 2β CH), 3.90 (mt, 1H, 5β CH), 4.77 (d, J=5.5 Hz, 1H, 2α CH), 8.43 (broad s, 1H, =CH at 6), 8.61 (broad s, 1H, =CH at 3)·$α_D^{20}$=−62.4°±1.2 (c=0.5, water).

EXAMPLE 5

A solution of 5.0 g of L-gulose and 5.2 g of ammonium formate in 20 cm$^3$ of water is heated at reflux for 2 hours and then allowed to cool to room temperature. The mixture is concentrated under reduced pressure (2.7 kPa) at a temperature in the region of 50° C. The black pasty residue is taken up in methanol, triturated and filtered and the insoluble fraction is washed with methanol. The filtrate is concentrated under reduced pressure (2.7 kPa) at a temperature in the region of 50° C. to give 7.5 g of a brown oil. The latter is purified by chromatography on a silica (0.020–0.045 mm) column, elution being carried out with an ethanol/n-butanol/ aqueous ammonia solution/water 8/2/2/1 by volume mixture. The fractions containing the expected product are combined and concentrated under reduced pressure (2.7 kPa) at a temperature in the region of 50° C., taken up successively in ethanol and ether and then reconcentrated. The oil obtained (0.6 g) is taken up in 5 cm$^3$ of water and then lyophilized. 0.47 g of 1-(6-(2S,3S,4-trihydroxybutyl) pyrazin-2-yl]butane-1R,2S,3S,4-tetraol is thus obtained in the form of a brown lyophilisate. $^1$H N.M.R. spectrum (400 MHz, d6-$(CD_3)_2SO$, at a temperature of 383 K, δ in ppm) 2.94 and 3.03 (2 dd, respectively J=14 and 9 Hz and J=14 and 4 Hz, each 1H, 6α $CH_2$), from 3.40 to 3.70 (mt, 6H, 2γ CH, 2δ $CH_2O$, 6γ CH and 6δ $CH_2O$), 3.88 (t, J=4 Hz, 1H, 2β CH), 4.01 (mt, 1H, 6β CH), 4.84 (d, J=4 Hz, 1H, 2α CH), 8.42 (s, 1H, =CH at 5), 8.57 (s, 1H, =CH at 3)·$α_D^{20}$ =−65.9°±−1.4 (c=0.5, water).

EXAMPLE 6

A solution of 5.0 g of L-glucose and 8.8 g of ammonium formate in 14 cm$^3$ of water is heated at reflux for 3 hours and then allowed to cool to room temperature. The mixture is concentrated under reduced pressure (2.7 kPa) at a temperature in the region of 65° C. The brown pasty residue is taken up in methanol, triturated and filtered and the insoluble fraction is washed with methanol. The filtrate is concentrated under reduced pressure (2.7 kPa) at a temperature in the region of 50° C. This operation is repeated in ethanol to give a brown oil (6.2 g). The latter is purified by chromatography on a silica (0.020–0.045 mm) column, elution being carried out with an ethanol/n-butanol/aqueous ammonia solution 8/2/1 by volume mixture. The fractions containing the expected product are combined and concentrated under reduced pressure (2.7 kPa) at a temperature in the region of 60° C. The oil obtained (0.5 g) is taken up in 14 cm$^3$ of ethanol, filtered while hot and then recrystallized. The crystals obtained are filtered, washed with ethanol and then pulled dry. After drying to constant weight at a temperature in the region of 40° C., 0.35 g of 1-[6-(2R,3S,4-trihydroxybutyl)pyrazin-2-yl]butane-1S,2R,3S,4-tetraol is obtained in the form of a beige crystalline solid melting at 114° C. (Rf=0.3; silica gel thin layer chromatography; eluent ethanol/n-butanol/aqueous ammonia solution/water 8/2/2/1 by volume mixture)].

EXAMPLE 7

A solution of 2.0 g of D-psicose and 3.2 g of ammonium formate in 3.4 cm$^3$ of water is heated at reflux for 2 hours and then allowed to cool to room temperature. The mixture is diluted with 25 cm$^3$ of ethyl acetate and separated by settling. The aqueous phase is washed with 25 cm$^3$ of ethyl acetate and then concentrated under reduced pressure (2.7 kPa) at a temperature in the region of 70° C. The brown oily residue is taken up in 100 cm$^3$ of ethanol, triturated and filtered and the insoluble fraction is washed with ethanol. The filtrate is concentrated under reduced pressure (2.7 kPa) at a temperature in the region of 45° C. to give a brown paste (1.6 g). The latter is purified by chromatography on a silica (0.020–0.045 mm) column, elution being carried out with an ethanol/water 199/1 by volume mixture, then by chromatography on a silica (0.020–0.045 mm) column, elution being carried out with an ethyl acetate/acetic acid/water 30/12/10 by volume mixture and finally by chromatography on a silica (0.020–0.045 mm) column at 4 pressure of approximately $1.5 \times 10^5$ Pa, elution being carried out with an ethanol/n-butanol/aqueous ammonia solution 8/2/1 by volume mixture. The fractions containing the expected product are combined and concentrated under reduced pressure (2.7 kPa) at a temperature in the region of 50° C. The amber solid obtained (0.22 g) is taken up in a mixture of 5 cm$^3$ of ethanol, and 0.25 cm$^3$ of water, filtered while hot and then recrystallized. The crystals obtained are filtered, washed with ethanol and then pulled dry. After drying to constant weight, 65.5 mg of 1-[5-(2S,3R,4-trihydroxybutyl)pyrazin-2-yl]-butane-1S,2S,3R,4-tetraol are obtained in the form of an ochre crystalline powder melting at 141° C. $^1$H N.M.R. spectrum (400 MHz, d6-(CD$_3$)$_2$SO, δ in ppm): 2.75 and 3.08 (2 dd, respectively J=14 and 10 Hz and J=14 and 2.5 Hz, each 1H, 5α CH$_2$), from 3.30 to 3.50 (mt, 4H, 2γ CH, 5γ CH, 1H of the 2δ CH$_2$O and 1H of the 5δ CH$_2$O), 3.60 (mt, 2H, the other H of the 2β CH$_2$O and the other H of the 5δ CH$_2$O), 3.79 (mt, 2H, 2β CH and 5β CH), 4.36 and 4.45 (2t, J=5.5 Hz, each 1H, OH at 2δ and OH at 5δ), 4.58, 4.64, 4.71 and 4.78 (4 d, respectively J=4.5 Hz, J=6.5 Hz, J=5 Hz and J=5.5 Hz, 4H, OH), 4.82 (t, J=5.5 Hz, 1H, 2α CH), 5.53 (d, J=5.5 Hz, 1H, OH at 2α), 8.41 (broad s, 1H, =CH at 6), 8.60 (broad s, 1H,=CH at 3).

EXAMPLE 8

A solution of 5.0 g of D-galactose and 8.8 g of ammonium formate in 14 cm$^3$ of water is heated at reflux for 45 minutes and then allowed to cool to room temperature. The mixture is diluted with 50 cm$^3$ of ethyl acetate and separated by settling. The aqueous phase is washed twice with 50 cm$^3$ of ethyl acetate and then concentrated under reduced pressure (2.7 kPa) at a temperature in the region of 65° C. The brown pasty residue is taken up in 100 cm$^3$ of ethanol and triturated and the supernatant is concentrated under reduced pressure (2.7 kPa) at a temperature in the region of 45° C. (operation repeated once). The residual brown solid is taken up successively in methanol, ethanol and then diethyl ether and evaporated to dryness under reduced pressure (2.7 kPa) at a temperature in the region of 45° C. The residue is purified by chromatography on a silica (0.020–0.045 mm) column at a pressure of approximately $1.5 \times 10^5$ Pa and while eluting with an ethanol/n-butanol/aqueous ammonia solution 8/2/1 by volume mixture. The fractions containing the expected product are combined and concentrated under reduced pressure (2.7 kPa) at a temperature in the region of 40° C. The yellow solid thus obtained (0.26 g) is taken up in a mixture of 3 cm$^3$ of ethanol and 0/25 cm$^3$ of water, filtered while hot and then recrystallized. The solid obtained is filtered and then pulled dry. After drying under reduced pressure (2.7 kPa) at a temperature in the region of 25° C., 119 mg of 1-[6-(2R,3R,4-trihydroxybutyl)pyrazin-2-yl]butane-1R,2R,3R,4-tetraol are obtained in the form of an amber pasty solid which melts at 90–130° C. (paste). $^1$H N.M.R. spectrum (400 MHz, d6-(CD$_3$)$_2$SO, δ in ppm): 2.89 (limit AB, 2H, 6α CH$_2$), from 3.30 to 3.55 (mt, 5H, 2δ CH$_2$O, 6δ CH$_2$O and 6γ CH), from 3.70 to 3.85 (mt, 2H, 2γ CH and 2β CH), 3.92 (mt, 1H, 6β CH), 4.64 (d, J=8.5 Hz, 1H, 2α CH), 8.38 (s, 1H, =CH at 5), 8.45 (s, 1H, =CH at 3).

The compounds of formula (I) exhibit advantageous pharmacological properties. They are of hypoglycaemic type.

The hypoglycaemic activity of the compounds of formula (I) was determined with respect to the hyperglycaemic response to the oral administration of glucose in the normoglycaemic mouse, according to the following protocol:

Swiss albino mice weighing between 22 and 26 g are left without nourishment for 2 hours. At the end of this period, the glycaemia is measured and, immediately after, a dose of glucose (2 g/kg) is administered orally. Thirty minutes later, the glycaemia is once again measured. The mice which respond by a hyperglycaemia greater than 170 mg/dl are selected and used to detect the hypoglycaemic activity of the compounds according to the invention.

The mice thus chosen are divided into groups of at least 10 animals. Several groups receive doses of 3 to 50 mg/kg of product in a vehicle, such as water or a mixture of methylcellulose/tween and water, once daily by gastric intubation. The treatment lasts 4 days. On the 4th day, after the final treatment, the animals receive a dose of glucose (2 g/kg) and the glycaemia is measured 20 to 40 minutes later. The percentage of inhibition of the hyperglycaemic response to the administration of glucose is calculated with respect to the response measured in the group treated with the vehicle.

In this test, the compounds according to the invention exhibit a percentage of inhibition of glycaemia of greater than or equal to 10%.

The compounds of general formula (I) according to the invention exhibit a low toxicity. Their LD$_{50}$ is greater than 2000 mg/kg via the oral route in the mouse.

In human therapeutics, these products are useful in the prevention and treatment of diabetes and in particular type II diabetes (NID disease), obese diabetes, diabetes at the age of about fifty, metaplethoric diabetes, diabetes affecting the elderly and mild diabetes. They can be used as a supplement to insulin therapy in insulin-dependent diabetes where they make it possible to gradually reduce the dose of insulin, unstable diabetes, insulin-resistant diabetes, and as a supplement to hypoglycaemic sulphamides when these do not provide a sufficient decrease in glycaemia. These products can also be used in complications of diabetes, such as hyperlipaemias, lipid metabolism disorders, dyslipaemias and obesity. They are also useful in the prevention and treatment of lesions of atherosclerosis and their complications (coronopathies, myocardial infarction, cardiomyopathies, progression of these three complications into left ventricular insufficiency, various arteriopathies, arterites of the lower limbs with claudication and progression into ulcers and gangrene, cerebral vascular insufficiency and its complications and sexual impotence of vascular origin), diabetic retinopathy and all its manifestations (increase in capillary permeability, capillary thrombosis and dilation, microaneurysms, arteriovenous shunt, venous dilation, punctiform and macular haemorrhages, exudates, macular oedemas, manifestations of proliferative retinopathy: neovessels, proliferative retinitis scars, haemorrhages of t he vitreous body, retinal detachment), diabetic cataract, diabetic neuropathy in its various forms (peripheral polyneuropathies and its manifestations such as paraesthesias, hyperaesthesias and pain, mononeuropathies, radiculopathies, autonomous neuropathies, diabetic amyotrophies), manifestations of diabetic foot (ulcers of the lower extremities and of the foot), diabetic nephropathy in its two diffuse and nodular forms, atheromatosis (rise in HDL lipoproteins promoting the elimination of cholesterol from the atheroma plaques, decrease in the LDL lipoproteins, decrease in the LDL/HDL ratio, inhibition of oxidation of the LDLs, decrease in plaque adhesiveness), hyperlipaemias and dyslipaemias (hypercholesterolaemias, hypertriglyceridaemias, normalization of the fatty acid level, normalization of uricaemia, normalization of the A and B apoproteins), cataracts, arterial hypertension and its consequences.

The medicaments according to the invention are composed of a compound according to the invention or a combination of these products, in the pure state or in the form of a composition in which it is combined with any other pharmaceutically compatible product, which can be inert or physiologically active. The medicaments according to the invention can be employed orally, parenterally, rectally or topically.

As solid compositions forloral administration, there can be used tablets, pills, powders (gelatin capsules, cachets) or granules. In these compositions, the active principle according to the invention is mixed with one or more inert diluents, such as starch, cellulose, sucrose, lactose or silica, under an argon stream. These composition can also comprise substances other than the diluents, for example one or more lubricants such as magnesium stearate or talc, a colorant, a coating (dragees) or a glaze.

As liquid compositions for oral administration, there can be used pharmaceutically acceptable solutions, suspensions, emulsions, syrups and elixirs containing inert diluents, such as water, ethanol, glycerol, vegetable oils or liquid paraffin. These compositions can comprise substances other than the diluents, for example wetting, sweetening, thickening, flavouring or stabilizing products.

The sterile compositions for parenteral administration can preferably be solutions in aqueous or nonaqueous form, suspensions or emulsions. As solvent or vehicle, there can be employed water, propylene glycol, a polyethylene glycol, vegetable oils, in particular olive oil, injectable organic esters, for example ethyl oleate, or other suitable organic solvents. These compositions can also contain adjuvants, in particular wetting, dsotonizing, emulsifying, dispersing and stabilizing agents. Sterilization can be performed in several ways, for example by aseptizing filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration can be, for example, creams, lotions, collyria, collutoria, nose drops or aerosols.

The doses depend on the desired effect, the duration of treatment and the administration route used; they are generally between 150 mg and 600 mg per day via the oral route for an adult with unit doses ranging from 50 mg to 200 mg of active substance.

In general, the doctor will determine the appropriate dosage according to the age, weight and all other factors specific to the subject to be treated.

The following examples illustrate compositions according to the invention:

EXAMPLE A

Hard gelatin capsules, with doses of 50 mg of active product, having the following composition are prepared according to the usual technique:

Active product . . . 50 mg

Cellulose . . . 18 mg

Lactose . . . 55 mg

Colloidal silica . . . 1 mg

Sodium carboxymethylstarch . . . 10 mg

Talc . . . 10 mg

Magnesium stearate . . . 1 mg

EXAMPLE B

Tablets, with doses of 50 mg of active product, having the following composition are prepared according to the usual technique:

Active product . . . 50 mg

Lactose . . . 104 mg

Cellulose . . . 40 mg

Polyvidone . . . 10 mg

Sodium carboxymethylstarch . . . 22 mg

Talc . . . 10 mg

Magnesium stearate . . . 2 mg

Colloidal silica . . . 2 mg

Hydroxymethylcellulose, glyqerol, titanium oxide (72/3.5/24.5) mixture qs for 1 finished film-coated tablet containing 245 mg

EXAMPLE C

An injectable solution containing 50 mg of active product having the following composition is prepared:

Active product . . . 50 mg

Benzoic acid . . . 80 mg

Benzyl alcohol . . . 0.06 ml

Sodium benzoate . . . 80 mg

Ethanol at 95% . . . 0.4 ml

Sodium hydroxide . . . 24 mg

Propylene glycol . . . 1.6 ml

Water . . . qs for 4 ml

The invention also relates to the use of the compounds of general formula (I) in the preparation of pharmaceutical compositions of use in the treatment or prevention of diabetes and complications of diabetes.

What is claimed is:

1. A pharmaceutical composition comprising at least one stereoisomer of at least one compound selected from the group consisting of

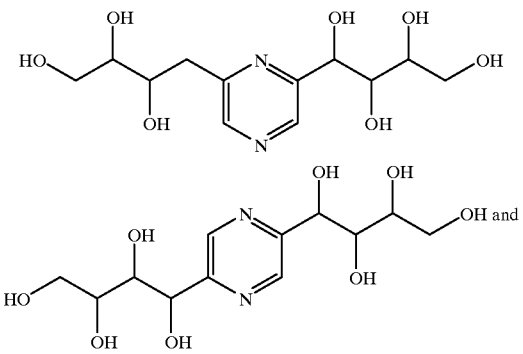

-continued

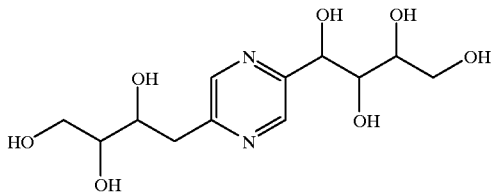

or a salt thereof with an organic or inorganic acid, provided however, that said compound is not fructosazine of formula:

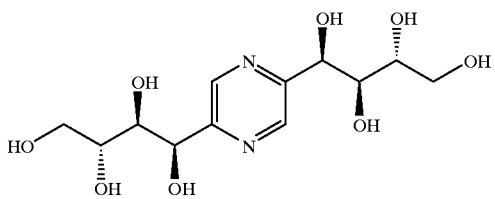

deoxyfructosazine of formula:

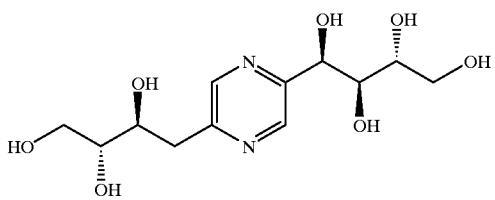

or the compound of formula:

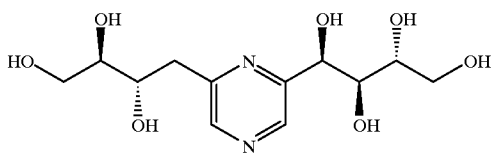

2. A pharmaceutical composition according to claim 1 comprising a compound selected from the group consisting of:

1-[5-(1R,2R,3R,4-tetrahydroxybutyl)pyrazin-2-yl]butane-1R,2R,3R,4-tetraol

1-[5-(1R,2R,3S,4-tetrahydroxybutyl)pyrazin-2-yl]butane-1R,2R,3S,4-tetraol

1-[5-(1R,2S,3S,4-tetrahydroxybutyl)pyrazin-2-yl]butane-1R,2S,3S,4-tetraol

1-[5-(1S,2R,3R,4-tetrahydroxybutyl)pyrazin-2-yl]butane-1S,2R,3R,4-tetraol

1-[5-(1S,2R,3S,4-tetrahydroxybutyl)pyrazin-2-yl]butane-1S,2R,3S,4-tetraol

1-[5-(1S,2S,3R,4-tetrahydroxybutyl)pyrazin-2-yl]butane-1S,2S,3R,4-tetraol

1-[S-(1S,2S,3S,4-tetrahydroxybutyl)pyrazin-2-yl]butane-1S,2S,3S,4-tetraol

1-[5-(2R,3R,4-trihydroxybutyl)pyrazin-2-yl]butane-1R,2R,3R,4-tetraol

1-[5-(2R,3S,4-trihydroxybutyl)pyrazin-2-yl]butane-1R,2R,3S,4-tetraol

1-[5-(2S,3S,4-trihydroxybutyl)pyrazin-2-yl]butane-1R,2S,3S,4-tetraol

1-[5-(2R,3R,4-trihydroxybutyl)pyrazin-2-yl]butane-1S,2R,3R,4-tetraol

1-[5-(2R,3S,4-trihydroxybutyl)pyrazin-2-yl]butane-1S,2R,3S,4-tetraol

1-[5-(2S,3R,4-trihydroxybutyl)pyrazin-2-yl]butane-1S,2S,3R,4-tetraol

1-[5-(2S,3S,4-trihydroxybutyl)pyrazin-2-yl]butane-1S,2S,3S,4-tetraol

1-[6-(2R,3R,4-trihydroxybutyl)pyrazin-2-yl]butane-1R,2R,3R,4-tetraol

1-[6-(2R,3S,4-trihydroxybutyl)pyrazin-2-yl]butane-1R,2R,3S,4-tetraol

1-[6-(2R,3R,4-trihydroxybutyl)pyrazin-2-yl]butane-1S,2R,3R,4-tetraol

1-[6-(2R,3S,4-trihydroxybutyl)pyrazin-2-yl]butane-1S,2R,3S,4-tetraol

1-[6-(2S,3R,4-trihydroxybutyl)pyrazin-2-yl]butane-1S,2S,3R,4-tetraol

1-[6-(2S,3S,4-trihydroxybutyl)pyrazin-2-yl]butane-1S,2S,3S,4-tetraol or a salt of such a compound with an inorganic or organic acid.

3. A compound selected from the group consisting of stereoisomers of compounds having the formula:

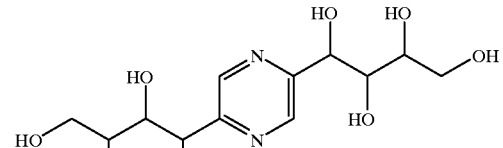

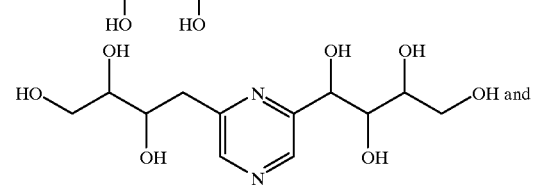

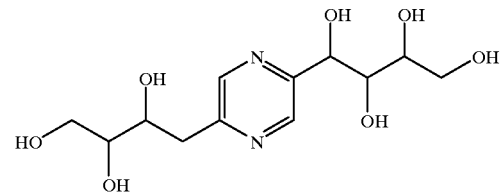

or a salt thereof with an inorganic or organic acid, provided, however, that said compound is not a compound having any of the following structures:

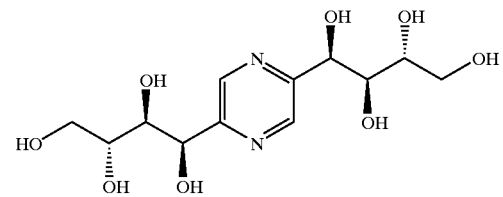

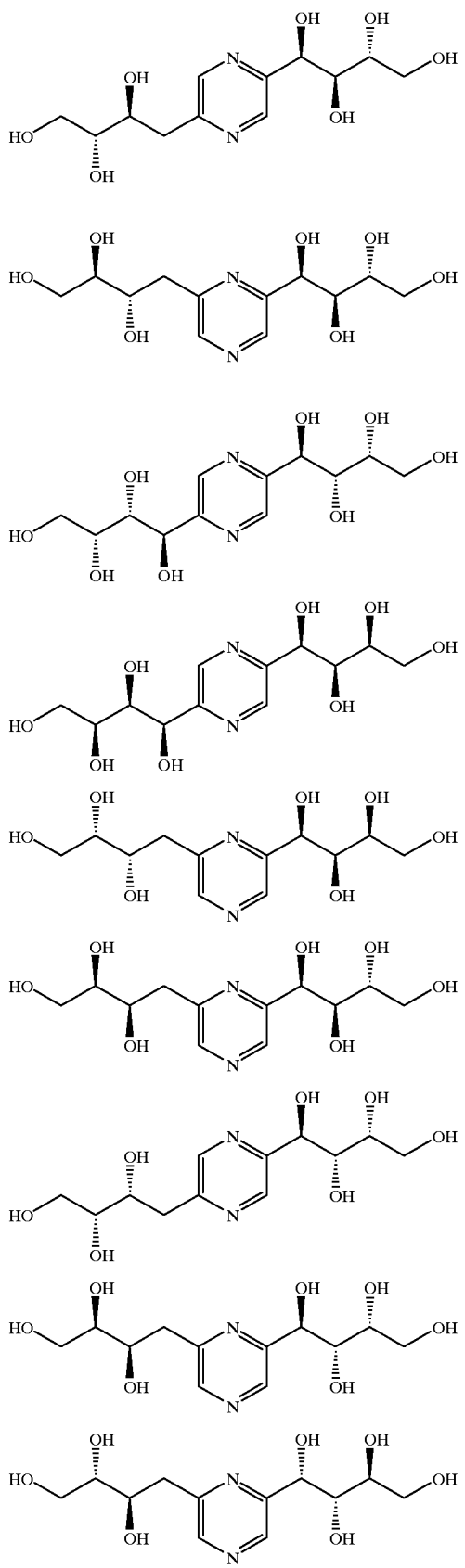
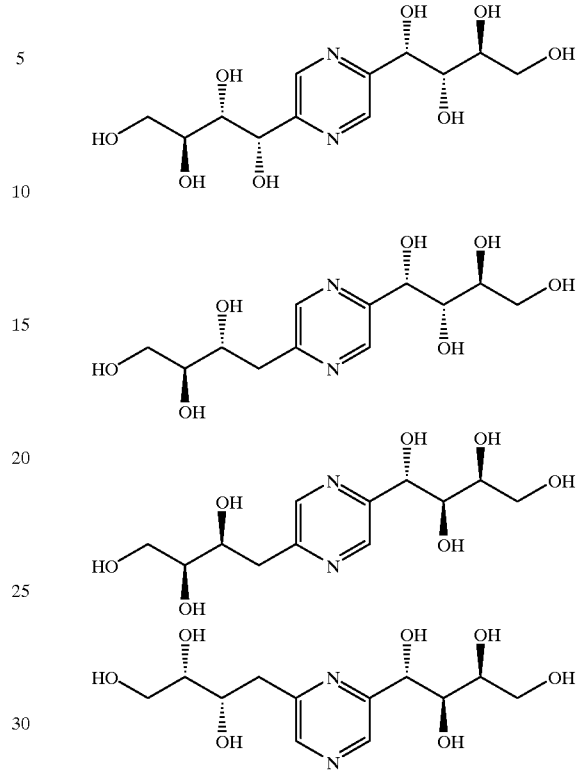

4. A compound according to claim 3 selected from the group consisting of:
1-[5-(1R,2R,3S,4-tetrahydroxybutyl)pyrazin-2-yl]butane-1R,2R,3S,4-tetraol
1-[5-(1S,2R,3R,4-tetrahydroxybutyl)pyrazin-2-yl]butane-1S,2R,3R,4-tetraol
1-[5-(1S,2S,3R,4-tetrahydroxybutyl)pyrazin-2-yl]butane-1S,2S,3R,4-tetraol
1-[5-(1S,2S,3S,4-tetrahydroxybutyl)pyrazin-2-yl]butane-1S,2S,3S,4-tetraol
1-[5-(2R,3S,4-trihydroxybutyl)pyrazin-2-yl]butane-1R,2R,3S,4-tetraol
1-[5-(2S,3S,4-trihydroxybutyl)pyrazin-2-yl]butane-1R,2S,3S,4-tetraol
1-[5-(2R,3R,4-trihydroxybutyl)pyrazin-2-yl]butane-1S,2R,3R,4-tetraol
1-[5-(2S,3R,4-trihydroxybutyl)pyrazin-2-yl]butane-1S,2S,3R,4-tetraol
1-[6-(2R,3S,4-trihydroxybutyl)pyrazin-2-yl]butane-1R,2R,3S,4-tetraol
1-[6-(2R,3R,4-trihydroxybutyl)pyrazin-2-yl]butane-1S,2R,3R,4-tetraol and
1-[6-(2S,3R,4-trihydroxybutyl)pyrazin-2-yl]butane-1S,2S,3R,4-tetraol
or a salt of such a compound with an inorganic or organic acid.

5. A compound according to claim 3 selected from the group consisting of:
1-[5-(2S,3S,4-trihydroxybutyl)pyrazin-2-yl]butane-1R,2S,3S,4-tetraol
1-[5-(2R,3R,4-trihydroxybutyl)pyrazin-2-yl]butane-1S,2R,3R,4-tetraol
1-[5-(2S,3R,4-trihydroxybutyl)pyrazin-2-yl]butane-1S,2S,3R,4-tetraol
and their salts with an inorganic or organic acid.

6. A process according to claim 5 wherein said ketose of formula (XII) is selected from D-psicose, D-sorbose, D-tagatose, L-psicose, L-fructose, L-sorbose and L-tagatose.

7. A process for the preparation of a stereoisomeric form of a compound having a formula:

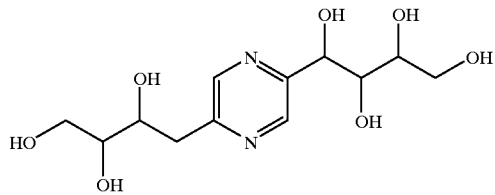

said process comprising reacting a ketose, or a mixture of two ketoses, of general formula $HOCH_2—CO—(CHOH)_3—CH_2OH$, with ammonium formate and isolating the product and optionally converting the product to a salt with an inorganic or organic acid.

8. A method for the treatment or prevention of diabetes or complications of diabetes, comprising administering to a patient in need of such treatment an effective amount of the compound of claim 1.

* * * * *